(12) United States Patent
Shankle et al.

(10) Patent No.: US 9,367,666 B2
(45) Date of Patent: Jun. 14, 2016

(54) MAPPING COGNITIVE TO FUNCTIONAL ABILITY

(75) Inventors: William Rodman Shankle, Corona del Mar, CA (US); Michael D. Lee, Irvine, CA (US); James P. Pooley, Irvine, CA (US)

(73) Assignee: Medical Care Corporation, Newport Beach, CA (US)

( * ) Notice: Subject to any disclaimer, the term of this patent is extended or adjusted under 35 U.S.C. 154(b) by 979 days.

(21) Appl. No.: 13/549,128

(22) Filed: Jul. 13, 2012

(65) Prior Publication Data
US 2014/0019059 A1 Jan. 16, 2014

(51) Int. Cl.
*G06G 7/48* (2006.01)
*G06F 19/00* (2011.01)
*A61B 5/16* (2006.01)

(52) U.S. Cl.
CPC ............ *G06F 19/345* (2013.01); *A61B 5/16* (2013.01); *G06F 19/3437* (2013.01)

(58) Field of Classification Search
CPC ...... G06F 19/345; G06F 19/3437; A61B 5/16
USPC ............................................................ 703/6
See application file for complete search history.

(56) References Cited

U.S. PATENT DOCUMENTS

2009/0155754 A1* 6/2009 Shankle et al. ............... 434/236
2011/0028827 A1* 2/2011 Sitaram et al. ............... 600/410

OTHER PUBLICATIONS

David Heeger, "Signal Detection Theory", Psychology Department, NYU, Nov. 12, 1997, pp. 1-10, http://www.cns.nyu.edu/~david/handouts/sdt-advanced.pdf.
Shankle et al., "Relating Memory to Functional Performance in Normal Aging to Dementia Using Hierarchical Bayesian Cognitive Processing Models", Alzheimer Dis Assoc Disord, vol. 00, No. 00, Lippincott Williams & Wilkins, 2012, pp. 1-7.
Reisberg et al., "Staging Dementia", in Principles and Practice of Geriatric Psychiatry, Second Edition, edited by Copeland et al., Copyright 2002, John Wiley & Sons Ltd., pp. 142-145.
Sclan et al., "Functional Assessment Staging (FAST0 n Alzheimer's Disease: Reliability, Validity, and Ordinality", International Psychogeriatrics, vol. 4, Supp. 1, 1992, pp. 55-69.

* cited by examiner

*Primary Examiner* — Dwin M Craig
(74) *Attorney, Agent, or Firm* — Fish & Richardson P.C.

(57) ABSTRACT

Methods, systems, and apparatus, including medium-encoded computer program products, for mapping cognitive to functional ability include receiving data regarding assessments of a cognitive ability and assessments of a functional ability; processing the received data to generate a map of one or more cognitive processes underlying the cognitive ability to a continuous-valued measure of the functional ability; and storing the generated map on a computer-storage medium to be used by a computer device in continuous-valued assessments of the functional ability.

26 Claims, 8 Drawing Sheets

TABLE 1. Number of Study Patients and Patient Assessments in Each FAST Stage

| FAST Stage | Patients | | Assessments | | Severity | FAST Stage* | |
|---|---|---|---|---|---|---|---|
| | N | % | N | % | | | Description |
| 1 | 159 | 15% | 288 | 19% | Normal | | No subjective or objective, cognitively related functional decline |
| 2 | 163 | 19% | 308 | 20% | Normal/SCI | | Subjective decline in cognitively related functional capacity |
| 3 | 26 | 36% | 129 | 9% | MCI | | Objective impairment in cognitively related complex functions without impairment in instrumental ADLs |
| 4 | 75 | 25% | 436 | 29% | Mild dementia | | Impaired instrumental ADLs |
| 5 | 47 | 7% | 189 | 12% | Moderate dementia | | Impaired judgment related to proper selection of clothing for social and weather conditions |
| 6 | 44 | 4% | 164 | 11% | Moderately severe dementia | | Impaired basic ADLs |
| All | 514 | 100% | 1514 | 100% | | | |

FIG. 3A

MAPPING COGNITIVE TO FUNCTIONAL ABILITY

BACKGROUND

This specification relates to mapping cognitive to functional ability, such as can be done based on results of a cognitive test and on results of a functional test that have been administered to multiple patients.

An example of a cognitive ability is episodic recall. For instance, episodic recall can be tested using a questionnaire about an individual's ability to do memory related tasks, such as remembering details of a recent conversation, remembering recent events, remembering when to take medications, and remembering to go to some future appointment. Results of this cognitive test include a subject's responses to the questionnaire—and represent subjective data. Episodic recall also can be tested using a memory task in which the subject is asked to learn a list of items, then, after several minutes delay or longer, to recall them with or without cues. Results of the latter cognitive test include a subject's responses to the memory task—and represent objective data.

An example of a measure of a functional ability is a questionnaire that asks how a range of tasks are performed—from an individual's most complex ones, to extremely simple tasks, such as walking, bathing, toileting, continence, truncal control, ability to smile, swallow, and hold up one's head. Such a measure of functional ability will be referred to, interchangeably, as a functional severity measure. Such functional ability tests can classify patients in categories corresponding into discrete values of the functional severity measure. Examples of such discrete functional severity measures include the Clinical Dementia Rating Scale, The Alzheimer's Disease Cooperative Study Activities of Daily Living Scale, and the Functional Assessment Staging Test (FAST) Procedure.

Typically, cognitive and functional abilities have been related to one another by computing their correlations. Such correlations indicate if a change in cognition is associated with a change in function or vice versa.

SUMMARY

This specification describes technologies relating to determining a form of a mapping between one or more cognitive processes—whose values differ for different levels of a discrete measure of functional severity—and a continuous measure of functional severity. Cognitive processes can be directly observed and measured or they can be latent. Latent cognitive processes are not directly measurable, but are indirectly inferred or estimated from the data. Regardless of whether cognitive processes are directly observed or latent, they can be mapped to different levels of a discrete measure of functional severity, which can be subsequently transformed into a continuous one. The systems and techniques described in this specification use latent cognitive processes to illustrate how this mapping can take place. However, both directly measured and latent cognitive processes can be used with the systems and techniques of this specification to map cognitive to functional abilities. The determined form of the mapping can be used to test for a causal relationship and to discover the continuum underlying the discrete functional severity measure. For instance, the systems and techniques described in this specification can be used to translate the one or more latent cognitive processes underlying performance of a cognitive task, into a continuous-valued measure of functional ability to perform a range of tasks. An example of two latent cognitive processes that underlie the cognitive task of episodic recall is 1) encoding of the stimulus, and 2) retrieval of the stimulus.

The systems and techniques described in this specification can be used to determine how cognition affects functional abilities. Such determination is important in Alzheimer disease and related disorders. In one example case study described in detail below, a total of 280 patients (normal or with Alzheimer disease and related disorders) received a total of 1514 assessments using the functional assessment staging test (FAST) procedure and the MCI Screen—a test of cognitive abilities. A hierarchical Bayesian cognitive processing model can be generated by embedding a signal detection theory (SDT) model of the MCI Screen-delayed recognition memory task into a hierarchical Bayesian framework. The signal detection theory model can use latent cognitive processing parameters of discriminability (representing a memory process) and response bias (representing an executive function) to predict, concurrently, recognition memory performance for each patient and each FAST severity group. In this example case study, the observed recognition memory data cannot distinguish the 6 FAST severity stages, but the latent cognitive processing parameters—determined in accordance with the disclosed technologies—completely separated them. The latent cognitive processing parameters can also be used to transform the ordinal FAST measure into a continuous measure reflecting the underlying continuum of functional severity. The Hierarchical Bayesian cognitive processing models described in this specification can be applied to recognition memory data from clinical practice settings to translate a latent measure of cognition into a continuous measure of functional severity for both individuals and FAST groups. Such a translation links two levels of brain information processing and may enable more accurate correlations with other levels, such as those characterized by biomarkers.

In general, an aspect of the subject matter described in this specification can be embodied in methods that include receiving data regarding assessments of a cognitive ability and assessments of a functional ability; processing the received data to generate a map of one or more cognitive processes underlying the cognitive ability to a continuous-valued measure of the functional ability; and storing the generated map on a computer-storage medium to be used by a computer device in continuous-valued assessments of the functional ability.

These and other embodiments can optionally include one or more of the following features. The one or more cognitive processes underlying the cognitive ability can include at least one of a directly measurable cognitive process or a latent cognitive process, where the latent cognitive process can be inferred from the received data. Further, the functional ability can be related to the cognitive ability. The generated map can be used to determine a rate of change in the functional ability. In addition, the generated map can be used to monitor continuous decline or improvement over time of the functional ability.

Processing the received the data to generate the map can include modeling the one or more cognitive processes underlying the cognitive ability, based on the received data and a cognitive processing model, in accordance with a discrete-valued measure of the functional ability, and generating the map of the one or more cognitive processes to the continuous-valued measure of the functional ability such that the generated map is anchored by the discrete-valued measure of the functional ability.

In some implementations, the processing can include iteratively performing the actions of (i) adjusting the cognitive processing model based on the map of the one or more cognitive processes to the continuous-valued measure of the functional ability, (ii) remodeling the one or more cognitive processes, based on the received data and the adjusted cognitive processing model, in accordance with the discrete-valued measure of the functional ability, and (iii) regenerating the map of the one or more cognitive processes to the continuous-valued measure of the functional ability, until convergence of the remodeling and the regenerating is obtained.

In some implementations, the modeling can include indicating how the one or more cognitive processes predict the received data; estimating values of parameters of the one or more cognitive processes from indications by the cognitive processing model of how the one or more cognitive processes predict the received data; and grouping values of at least one of the parameters of the one or more cognitive processes in groups corresponding to values of the discrete-valued measure of the functional ability. The cognitive ability can include a delayed recognition memory task. The one or more cognitive processes underlying the delayed recognition memory task can include latent cognitive processes such as memory strength and judgment. A parameter of memory strength can include discriminability and a parameter of judgment can include response bias.

Generating of the map can include estimating a continuous functional relationship that fits the grouped values of the at least one of the parameters of the one or more cognitive processes and the values of the discrete-valued measure of the functional ability. Further, the continuous functional relationship can include a parametric psychophysical function having multiple parameters that control at least a baseline, potential change and a shape of the parametric psychophysical function. Furthermore, estimating the reliability of the continuous functional relationship can include one or more of Markov Chain Monte Carlo sampling, bootstrapping or permutation sampling. Moreover, the methods can include indicating individual predictions of the received data based on individual values of the at least one of the parameters of the one or more cognitive processes and group predictions of the received data based on grouped values of the parameters of the one or more cognitive processes, and comparing the indicated individual and group predictions to determine a cognitive difference of an individual associated with the individual prediction relative to a group of individuals associated with the group prediction.

In some implementations, the cognitive processing model can include a combination of a signal detection theory model and a Bayesian analysis. In some implementations, the discrete-valued measure of the functional ability can include one or more of the Clinical Dementia Rating Scale, the Alzheimer's Disease Cooperative Study Activities of Daily Living Scale or the Functional Assessment Staging Test Procedure.

In general, another aspect of the subject matter described in this specification can be embodied in a system that includes one or more hardware processors, and a storage system storing instructions that, when executed by the one or more hardware processors, cause the system to perform operations including receiving data regarding assessments of delayed recognition memory and assessments of a functional severity, and modeling discriminability as a parameter of memory strength and response bias as a parameter of judgment. The memory strength and the judgment are latent cognitive processes underlying the delayed recognition memory. The discriminability and response bias are modeled based on the received data and a cognitive processing model, in accordance with a discrete-valued measure of the functional severity. The operations performed by the system further include generating a map of the discriminability to a continuous-valued measure of the functional severity such that the generated map is anchored by the discrete-valued measure of the functional severity, and storing the map for use by the system in a continuous-valued assessment of the functional severity.

These and other embodiments can optionally include one or more of the following features. In some implementations, the cognitive processing model can include a combination of a signal detection theory model and a Bayesian analysis. In some implementations, the discrete-valued measure of the functional severity can include one or more of the Clinical Dementia Rating Scale, the Alzheimer's Disease Cooperative Study Activities of Daily Living Scale or the Functional Assessment Staging Test Procedure. In some implementations, the functional severity can be related to the delayed recognition memory. In some implementations, the system can use the generated map to determine a rate of the functional severity, for example; or to monitor continuous decline or improvement over time of the functional severity, as another example.

The instructions, when executed by the one or more hardware processors, can cause the system to iteratively perform operations including (i) adjusting the cognitive processing model based on the map of the discriminability to the continuous-valued measure of the functional severity, (ii) remodeling the discriminability and the response bias, based on the received data and the adjusted cognitive processing model, in accordance with the discrete-valued measure of the functional severity, and (iii) regenerating the map of the discriminability to the continuous-valued measure of the functional severity, until convergence of the remodeling and the regenerating is obtained.

In some implementations, the operation of modeling can include indicating how the discriminability and the response bias predict the received data; estimating values of the discriminability and values of the response bias from indications by the cognitive processing model of how the discriminability and the response bias predict the received data; and grouping the values of the discriminability and the values of the response bias in groups corresponding to values of the discrete-valued measure of the functional severity. The operation of generating the map can include estimating the reliability of the continuous-valued functional relationship that fits the grouped values of the discriminability and discrete values of the functional severity measure. For instance, the continuous functional relationship can include a parametric psychophysical function having multiple parameters that control at least a baseline, potential change and a shape of the parametric psychophysical function. The operation of estimating the reliability of the continuous-valued functional relationship can include one or more of Markov Chain Monte Carlo sampling, bootstrapping or permutation sampling.

In addition, the operations performed by the system can include indicating individual predictions of the received data based on individual values of the discriminability and the response bias and group predictions of the received data based on grouped values of the discriminability and the response bias, and comparing the indicated individual and group predictions to determine a cognitive difference of an individual associated with the individual prediction relative to a group of individuals associated with the group prediction.

Particular embodiments of the subject matter described in this specification can be implemented to realize one or more of the following advantages. The disclosed technologies can be used to improve the measurement and assessment of changes in normal aging, a transition from normal aging to a disease condition, and disease progression. The types of models and item responses can include measures of affective or emotional, sensory perceptual, attentional, cognitive, functional, neurological, behavioral, and social abilities.

A potentially useful clinical application of the disclosed systems and techniques is that delayed recognition memory tasks can be used to create a continuous measure of severity of functional impairment that reliably predicts FAST staging, which is an ordinal measure. A continuous measure of functional severity allows one to compute the rate of functional decline, which can be used, for example, to determine whether a treatment has delayed disease progression.

A psychophysical function used to model the relationship between discriminability and the FAST stages, as described in this specification, can aid the interpolation, generalization, and prediction of the severity of functional impairment. In other words, this psychophysical function allows one to trace out trajectories of functional decline with respect to discriminability and map these trajectories into statements about memory task performance. For example, in vascular cognitive impairment and dementia, the rate of change in the discriminability cognitive processing parameter underlying delayed recognition memory task performance declines more slowly as functional severity progresses than in Alzheimer's Disease, Lewy Body Disease or multiple causes of cognitive impairment and dementia.

The technologies disclosed in this specification demonstrate how one can concurrently evaluate clinically relevant groups (e.g., FAST stage groups) and individuals within each group. For instance, the described techniques can predict the distribution of an individual's recognition memory performance better than that obtained by the individual's group-level predictions. This is particularly useful for patients who may belong to a distinct subset of the distribution.

The systems and techniques described in this specification also show how latent processes of memory and executive function that are not directly measurable can be usefully estimated from the delayed recognition memory response data. For instance, the distributions of the means of these latent parameters for the different FAST stages are completely separated, whereas the observed recognition memory data does not separate the FAST stages. This improved separation of the FAST stages illustrates a potentially important advantage of the disclosed generative hierarchical Bayesian cognitive processing (HBCP) models over discriminative statistical methods.

In addition, the disclosed technologies can accurately translate a measure of cognition into a continuous measure of the degree of impairment in functional capabilities. This translational ability may facilitate better understanding of the relations between cognition, function, and other levels of brain information processing, including those measured by biomarkers at molecular, structural, and electrophysiological levels.

The ability to translate brain processes mediating cognitive abilities into brain processes mediating functional abilities helps identify the practical importance of cognition, which is useful for robotics, the study of complex adaptive systems, for evaluating the effect of a treatment in various disorders affecting the brain.

The details of one or more embodiments of the subject matter described in this specification are set forth in the accompanying drawings and the description below. Other features, aspects, and advantages of the invention will become apparent from the description, the drawings, and the claims.

BRIEF DESCRIPTION OF THE DRAWINGS

FIG. 3A shows example assessments of functional severity using a discrete-valued measure.

Like reference numbers and designations in the various drawings indicate like elements.

DETAILED DESCRIPTION

Figure 1:
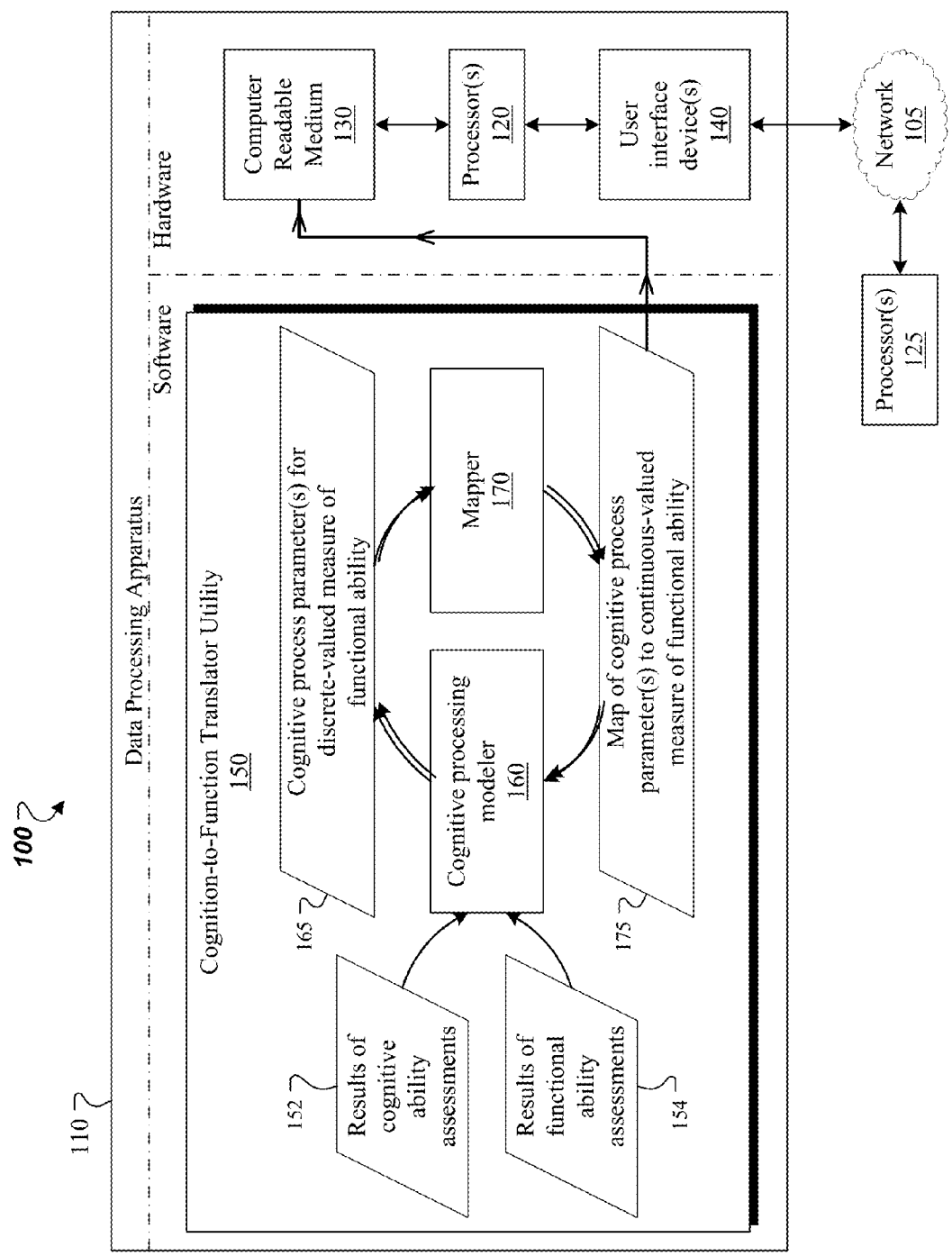
FIG. 1 shows an example system used to generate a mapping of cognitive to functional ability.

FIG. 1 shows an example system 100 used to generate a mapping of cognitive to functional ability. A data processing apparatus 110 can include hardware/firmware and one or more software programs, including a cognition-to-function translator utility 150. The cognition-to-function translator utility 150 operates in conjunction with the data processing apparatus 110 to effect various operations described in this specification. The cognition-to-function translator utility 150, in combination with the various hardware, firmware, and software components of the data processing apparatus 110, represent one or more structural components in the system 100, in which the algorithms described herein, can be embodied. For instance, the cognition-to-function translator utility 150 can be an application for generating a map 175 of one or more cognitive process parameters to a continuous-valued measure of functional ability. A computer application refers to a computer program that the user perceives as a distinct computer tool used for a defined purpose. An application can be built entirely into an operating system or other operating environment, or it can have different components in different locations (e.g., a remote server). In any case, the cognition-to-function translator utility 150 can generate the map 175 based on data regarding assessments of cognitive ability 152 and data regarding assessments of functional ability 154, where the data 152, 154 corresponds to one or more subjects.

The cognition-to-function translator utility 150 can include or interface with other software such as database software, testing administration software, data analysis/computational software, and user interface software, to name a few examples. User interface software can operate over a network to interface with other processor(s). For example, the cognition-to-function translator utility 150 can include software methods for inputting and retrieving data associated with a brain function test, such as score results corresponding to cognitive and functional tests, or demographic data. The cognition-to-function translator utility 150 can also effect various analytic processes, which are described further below.

The data processing apparatus includes one or more processors 120 and at least one computer-readable medium 130 (e.g., random access memory, storage device, etc.). The data processing apparatus 110 can also include one or more user interface devices 140. The user interface devices 140 can include display screen(s), keyboard(s), a mouse, stylus, modems or other networking hardware/firmware, or any combination thereof to name a few examples. The subject matter described in this specification can also be used in conjunction with other input/output devices, such as a printer or scanner. The user interface device 140 can be used to connect to a network 105, and can furthermore connect to a processor or processors 125 via the network 105 (e.g., the Internet).

Therefore, a user of the cognition-to-function translator utility 150 does not need to be local, and may be connecting using a web browser on a personal computer, or using other suitable hardware and software at a remote location. For example, a clinician at a testing center can access a web interface via the remote processor 125 in order to input test data for a given cognitive test, a particular functional test or both. The test data can be the results of an already administered test, or the test data can be the information exchanged when actually administering the test using a network based testing system. In any event, data can be transmitted over the network 105 to/from the data processing apparatus 110. Furthermore the clinician can input test data and retrieve analysis based on that data or other data stored in a database. Note that the data processing apparatus 110 can itself be considered a user interface device (e.g., when the cognition-to-function translator utility 150 is delivered by processor(s) 125 as a web service).

In the present example, the cognition-to-function translator utility 150 includes a cognitive processing modeler 160 and a mapper 170. Results of assessments of a cognitive ability 152 and results of assessments of a functional ability 154 can be received by the cognitive processing modeler 160. The cognitive ability results 152 can include subjective or objective observed data related to the assessed cognitive ability. The cognitive processing modeler 160 can construct a cognitive processing model to indicate how one or more cognitive processes underlying the assessed cognitive ability predicts (generates) the subjective or objective observed data 152 related to the assessed cognitive ability. In some implementations, signal detection theory can be integrated in a Hierarchical Bayesian Cognitive Processing Model framework to construct such a model. The functional ability results 154 can include subjective or objective observed data related to the assessed functional ability. The functional ability results 154 correspond to values of a discrete-valued (ordinal or binary) measure of the functional ability used to assess individuals. This discrete-valued measure provides anchor points on a scale, or benchmarks, of the underlying continuum of functional ability that can be discovered. In this manner, the cognitive processing modeler 160 can use the constructed cognitive processing model to model one or more cognitive processes underlying performance of the assessed cognitive ability, and to predict one or more parameters 165 of at least one modeled cognitive process for the discrete-valued measure of functional ability.

The mapper 170 can use the one or more parameters 165 output by the cognitive processing modeler 160 to generate the map 175 of the one or more cognitive processes to the continuous-valued measure of the functional ability. Moreover, the map 175 can be generated by the mapper 170 to be anchored by the discrete-valued measure of the functional ability. In some implementations, the mapper 170 can postulate and then test a cognition-to-function equation to generate a continuous-valued functional ability measure. One or more parameters 165 of the cognitive processes (modeled by the modeler 160 based on the observed data 152, 154 and the cognitive processing model, in accordance with the discrete-valued measure of the functional ability) are combined with the discrete-valued functional ability measure to postulate the equation. Psychophysical functions are analogous to the kinds of equations that may be useful to model the map 175 between cognition and function, as described below in this specification.

To assess reliability of the predicted values of the cognitive process parameters 165, various sampling methods (e.g., Markov Chain Monte Carlo sampling, bootstrapping or permutation sampling) can be used by the mapper 170 to sample the values of the cognitive process parameters 165 (modeled by the cognitive processing modeler 160 based on the observed data 152, 154 and the cognitive processing model, and in accordance with the discrete-valued measure of the functional ability) for every possible equation derived from parameters of the psychophysical function, given the observed data 152, 154, and the cognitive processing model used by the modeler 160. Differences between the values of the cognitive process parameters 165 as modeled by the cognitive processing modeler 160 or as predicted by the mapper 170 (expressed in terms of confidence intervals or credible intervals, as described in detail below) represent measures of the reliability of the continuous measure of functional ability.

To obtain a desired reliability of the continuous measure of functional severity, the cognition-to-function translator utility 150 can, iteratively, (i) instruct the cognitive processing modeler 160 to adjust the cognitive processing model based on the generated map 175; (ii) instruct the cognitive processing modeler 160 to remodel the one or more cognitive process parameters 165, based on the observed data 152, 154 and the adjusted cognitive processing model, in accordance with the discrete-valued measure of the functional ability; and (iii) instruct the mapper 170 to regenerate the map 175 of the one or more cognitive processes to the continuous-valued measure of the functional ability, until convergence of the remodeling and the regenerating is obtained. The convergence can be obtained when the confidence interval or a credible interval satisfies a target value, for instance.

The generated map 175 can be stored by the cognition-to-function translator utility 150 on the computer readable medium 130 to be used in a continuous-valued assessment of the functional ability. A reliable cognition-to-function equation underlying the stored map 175 can be used for a variety of purposes, including clinical trials, evaluation of patients in clinical practice and other settings, plus underwriting and claims assessment for life insurance, disability insurance or long-term care insurance.

Figure 2:
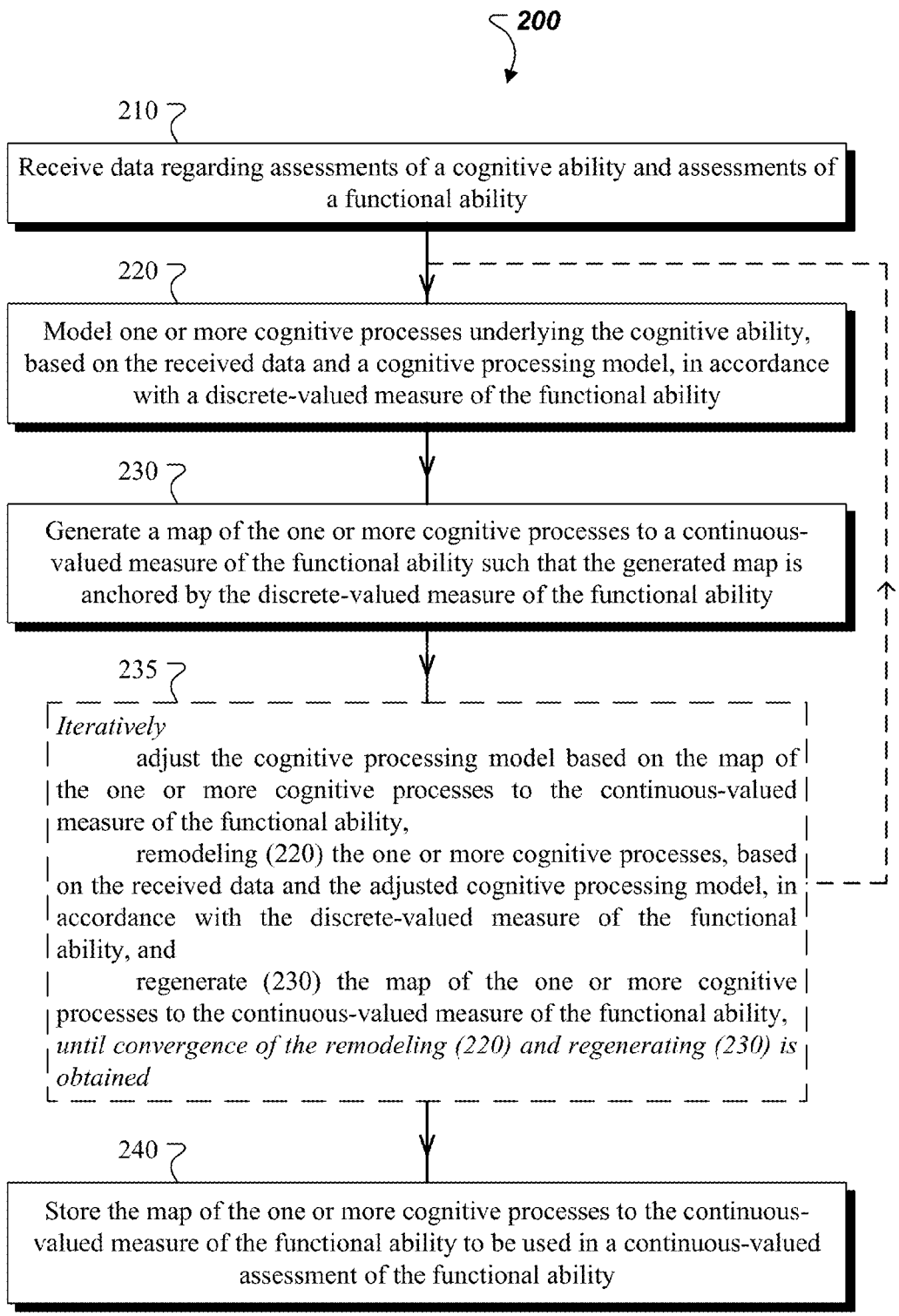
FIG. 2 shows an example process used to generate a mapping of cognitive to functional ability.

FIG. 2 shows an example process 200 used to generate a map of one or more cognitive processes underlying a cognitive ability onto a continuous-valued measure of functional ability. In some implementations, the process 200 can be performed by the system 100. Cognition can be related to function by computing their correlations. Such correlations can indicate if a change in cognition is associated with a change in function, or vice versa. However, such correlations do not translate the cognitive measure into a functional one. Correlations also do not specify any formal mechanism by which cognitive processes may predict, or even cause, a given level of a functional ability measure. In contrast, a model that posits a form of the relationship between one or more latent or directly observed cognitive processes—whose values differ for different levels of a discrete-valued measure of functional ability—and a continuous measure of functional ability provides the opportunity to test for a causal relationship and to discover the continuum underlying the discrete-valued functional ability measure.

The process 200 can model cognitive processes underlying a cognitive ability being studied. In this manner, the process 200 can provide useful insights into the cognitive ability, and can concurrently estimate parameters for groups and individuals, can automatically make inferences for missing data, and can integrate multidimensional data into a single construct. Such multidimensional data include, but are not limited to, biomarkers, subjective and objective cognitive, affective, behavioral and functional measures, plus potentially confounding covariates. In addition, the process 200 can also be used to predict the relations between the different types of abilities that the brain is capable of performing, such as the relationship between cognitive and functional abilities, between cognitive and affective abilities, cognitive and behavioral abilities, and so forth.

At 210, data regarding assessments of a cognitive ability and assessments of a functional ability is received. As noted above in connection with FIG. 1, the received data can be from previously administered tests or from one or more tests that are currently being administered. Nonetheless, the example process 200 and other implementations of the more general concepts underlying this example process (e.g., as described below in connection with FIGS. 3A-3B) are not practiced on the human body since such processes do not themselves involve an interaction necessitating the presence of the person.

At 220, one or more cognitive processes underlying the cognitive ability are modeled, based at least in part on the received data and a cognitive processing model, in accordance with a discrete-valued measure of the functional ability. In some implementations, the discrete-valued measure of the functional ability can include one or more of the Clinical Dementia Rating Scale, the Alzheimer's Disease Cooperative Study Activities of Daily Living Scale or the FAST Procedure. For instance, the FAST stages have previously been correlated with the degree of cognitive impairment.

In some implementations, the cognitive processing model can include a combination of a signal detection theory model and a Bayesian analysis. As part of applying the cognitive processing model to the received data, how the one or more cognitive processes predict the received data can be indicated. Values of parameters of the one or more cognitive processes can be evaluated from indications by the cognitive processing model of how the one or more cognitive processes predict the received data. Additionally, values of at least one of the parameters of the one or more cognitive processes can be grouped in groups corresponding to values of the discrete-valued measure of the functional ability. In this manner, how the discrete-valued measure of functional severity influences the cognitive processing parameters can be modeled. Corresponding levels of the discrete-valued measure of functional ability of each individual at the time of the cognitive ability assessment can be used to adjust the values of the cognitive processing parameters in the cognitive processing model. Thus, for different discrete levels of functional ability, the process 200 can determine different sets of values of the cognitive processing parameters.

In some cases, the cognitive ability can be a delayed recognition memory task. In such cases, one or more latent cognitive processes underlying the delayed recognition memory can be memory strength and judgment. For example, a parameter of the memory strength can be discriminability and a parameter of the judgment can be response bias, as described in detail in connection with FIGS. 3A-3B. In some other cases, the cognitive abilities can be judged comparisons, object naming, verbal fluency, and list learning. The corresponding cognitive processes of judging how two items differ from a third item, naming a presented object, generating a list of common nouns, and learning a series of items presented repeatedly can be directly observed and measured. The cognitive processing model used at 220 can include, for each of these directly observable and measureable cognitive processes, one or more parameters that can be influenced by age, gender, education, drug treatment, diagnosis, disease severity and other factors that would attempt to predict the performance of the associated cognitive process.

At 230, the map of the one or more cognitive processes to the continuous-valued measure of the functional ability is generated, such that the generated map is anchored by the discrete-valued measure of the functional ability. To develop a cognition-to-function equation, as part of the map generating, one or more of the cognitive processing parameters plus a discrete-valued measure of functional severity can be used to derive a mathematical function that infers or predicts a continuous-valued measure of functional severity. As such, a continuous functional relationship can be estimated—that fits the grouped values of the at least one of the parameters of the one or more cognitive processes and the values of the discrete-valued measure of the functional ability. For example, the continuous functional relationship can include a parametric psychophysical function having multiple parameters that control at least a baseline, a potential change and a shape of the parametric psychophysical function. As part of estimating the reliability of the continuous functional relationship, one or more of Markov Chain Monte Carlo sampling, bootstrapping or permutation sampling can be performed. To predict a cognitive processing parameter per each of the discrete ability stages, any of the above-noted sampling methods can be used to sample the values of the cognitive processing parameter generated by every possible curve derived from parameters of the psychophysical function, given the received data, and the cognitive processing model.

The parametric psychophysical function can be estimated to fit the modeled relation between one or more predicted cognitive processing parameters and the degree of impairment in functional capabilities as measured by the discrete-valued measure. In some implementations, this modeled relation can use fully Bayesian inference, which means that the joint distributions over the parameters of the psychophysical function and the group cognitive processing parameter values can be concurrently inferred. In this manner, the values between the discrete values of the functional severity measure can be inferred through the parametric psychophysical function. It is these inferred values between the discrete functional severity stage values that constitute the transformation of a discrete functional ability measure into a continuous one.

Further, individual predictions of the received data can be indicated based on individual values of the at least one of the parameters of the one or more cognitive processes and group predictions of the received data based on grouped values of the parameters of the one or more cognitive processes. Additionally, the indicated individual and group predictions can be compared to determine a cognitive difference of an individual associated with the individual prediction relative to a group of individuals associated with the group prediction.

Optionally at 235, the following sequence of actions can be performed iteratively: (i) the cognitive processing model is adjusted based on the map of the one or more cognitive processes to the continuous-valued measure of the functional ability; (ii) the one or more cognitive processes are remodeled, based on the received data and the adjusted cognitive processing model, in accordance with the discrete-valued measure of the functional ability; and (iii) the map of the one or more cognitive processes to the continuous-valued measure of the functional ability is regenerated, until convergence of the remodeling and the regenerating is obtained.

At 240, the generated map is stored on a computer-storage medium to be used by a computer device in a continuous-valued assessment of the functional ability. For example, the stored map can be used to determine a rate of the functional ability. As another example, the stored map can be used to monitor continuous decline or improvement over time of the functional ability. Moreover, the psychophysical function underlying the stored map enables tracing out trajectories of functional decline with respect to a cognitive processing parameter, and mapping of these trajectories into statements about memory task performance and functional severity.

As disclosed above in this specification, the process 200 uses a cognitive processing model in conjunction with a cognitive task, a discrete measure of functional severity (nominal, binary or ordinal), and a mathematical form of a relation between cognition and function to generate a continuous-valued functional severity measure from a cognitive measure and a discrete or ordinal functional one. An example of implementing the process 200 in the system 100 is described below for relating memory to functional performance in normal aging to dementia. Relating cognitive to functional ability has been a relatively understudied area in Alzheimer disease (AD) research. Yet, it is practically important in terms of understanding outcomes in clinical trials and in predicting the degree of impairment in functional capabilities from objective cognitive testing in clinical practice.

The usual way of relating cognition to function has been to look at their intercorrelations. An alternative approach is to create a model that posits the form of the relationship between the degree of impairment in functional capabilities and the processes underlying a given cognitive task. As described below in this specification, a methodology can be applied that combines hierarchical Bayesian statistical methods with psychological measurement models of the processes underlying memory (hierarchical Bayesian cognitive processing, (HBCP)). Such models may provide useful insights into the cognitive ability being studied. They can also concurrently estimate parameters for groups and individuals, automatically make inferences for missing data, and integrate multi-dimensional data, such as biomarkers, cognitive, and functional measures plus covariates, into a single construct.

A delayed recognition memory task may help relate cognitive and functional changes because its performance requires memory storage and executive function processes. The task involves studying a list of items (usually words or pictures) one or more times, and then after a few minutes or longer, presenting these studied (old) items intermixed with a list of non-studied (new) items. The subject is asked to discriminate the old from the new items.

Signal detection theory (SDT) can be used to model recognition memory as composed of underlying memory and decision-making processes. Decision making is an executive function, which helps individuals perform various functional abilities. The FAST procedure is a valid and internationally used measure of the degree of impairment in functional capabilities for persons with AD, in which the functional stages have been correlated with cognitive impairment. Because of their use in clinical practice and research, it is useful to explore how different degrees of functional incapacity relate to an SDT model of delayed recognition memory using clinical data.

FAST Staging Procedure:

At each patient visit, a trained physician can interview either the patient or a reliable informant using the FAST procedure to stage the patient's degree of functional incapacity into one of the 16 stages (7 major stages, 1 to 7, with 11 sub-stages, 6a to e and 7a to f). Patients with no subjective and no objectively evident functional impairment can be classified as FAST stage 1 and will be referred to as no cognitively related functional impairment (NCI). Patients who subjectively have greater difficulty in cognitively related functional abilities but still perform them completely normally can be classified as FAST stage 2. FAST stage 2 patients will be referred to as subjective cognitively related functional impairment (SCI). Patients who have impairment in cognitively related, executive-level functional abilities, such as using a calendar to prospectively keep appointments but have no impairment in instrumental activities of daily living (complex activities of daily life, managing personal finances properly, and preparing meals for guests, in one's accustomed manner), can be classified as FAST stage 3. FAST stage 3 patients will be referred to as mild cognitively related functional impairment (MCI). FAST stage 4, 5, and 6 patients have functional deficits that correspond to the levels of mild, moderate, and moderately severe dementia, respectively, and can be classified by their degree of impairment in instrumental and basic activities of daily living.

Cognitive Testing: At each visit, patients can be tested with a cognitive battery derived from the Consortium to Establish a Registry for AD (CERAD), consisting of trails A and B—measures of sequencing, processing speed, and set shifting; FAS letter fluency—a measure of phonemic fluency, working memory, and rule application; Ishihara number naming test—a measure of object recognition that minimizes the use of semantic memory; CERAD drawings—a measure of simple object recognition, planning, organization, and visual constructional praxis; and the MCI Screen (MCIS)—a measure of rule application, working memory, rehearsed delayed recall and recognition memory, unrehearsed delayed recall, judged comparisons, and self-estimation of memory ability. The MCIS was the only cognitive test involved in relating cognition to function for the example assessments described below in this specification, but other cognitive tests can be used.

FIG. 3A shows Table 1 that includes the numbers of patients and patient assessments by FAST stage, along with its description. The data for the example assessments described in this specification came from a primary care and a cognitive disorder clinic and included all assessments of 280 patients followed up every 3 to 6 months for up to 6 years. The number of patients assessed one or more times in any given FAST stage varied from 26 to 163. If one sums the number of patients assessed per FAST stage over the 6 stages, the total is 514, which is greater than the 280 patients in the study. This is because each patient can contribute data to one or more FAST stages. There was a total of 1514 FAST stage assessments for the 280 patients studied.

Because the data are repeated measures, there are potential confounding effects on task performance due to practice and reliability. However, these potential confounds have been shown to be small and are therefore unlikely to influence the present study's results (MCIS interrater and test-retest reliability=0.839; wordlist effect size<0.009 SDs11). Patients with AD or a related disorder (ADRD) underwent a standardized evaluation, including MRI, laboratory tests, medical history, and physical examination and were diagnosed according to the published criteria for AD, Lewy body disease, cerebrovascular disease, and frontal temporal lobe disease. Patients were followed up every 3 to 6 months from 2002 to 2007.

Delayed Recognition Memory Task:

The delayed recognition memory task was performed after the MCIS-delayed free recall task. The examiner can read aloud to the patient the 10 study list words (old) intermixed with 10 unstudied words (new), one at a time, and the patient is asked to decide whether the word was old or new. In SDT, correct identifications of old and new words are called hits and correct rejections; incorrect identifications of old and new words are called misses and false alarms.

Construction of New Wordlists for the MCIS:

Ten pairs of equivalent wordlists can be constructed to minimize practice effects, minimize inter-item associability, and parallel the original CERAD wordlist. Eight of the ten pairs can be used with the MCIS test. Each time a patient is tested, the MCIS algorithm can randomly select a pair of old and new wordlists from the available pool without replacement. This means that the patient has to take the MCIS test nine times before being exposed to the same pair of wordlists. The wordlists were designed so that: (1) the items of the old and new wordlists are similar; (2) words are 1 or 2 syllables; (3) their frequency, range, and diversity statistics resemble those of the original CERAD wordlist; (4) the words in each list are not easily associable (low semantic associability); (5) the residual semantic similarities among list words are comparable with those of the CERAD wordlist; and (6) neither homophones (e.g., bare/bear) nor words ending in the same phoneme (e.g., plain/airplane) are allowed in a wordlist.

Figure 3B:
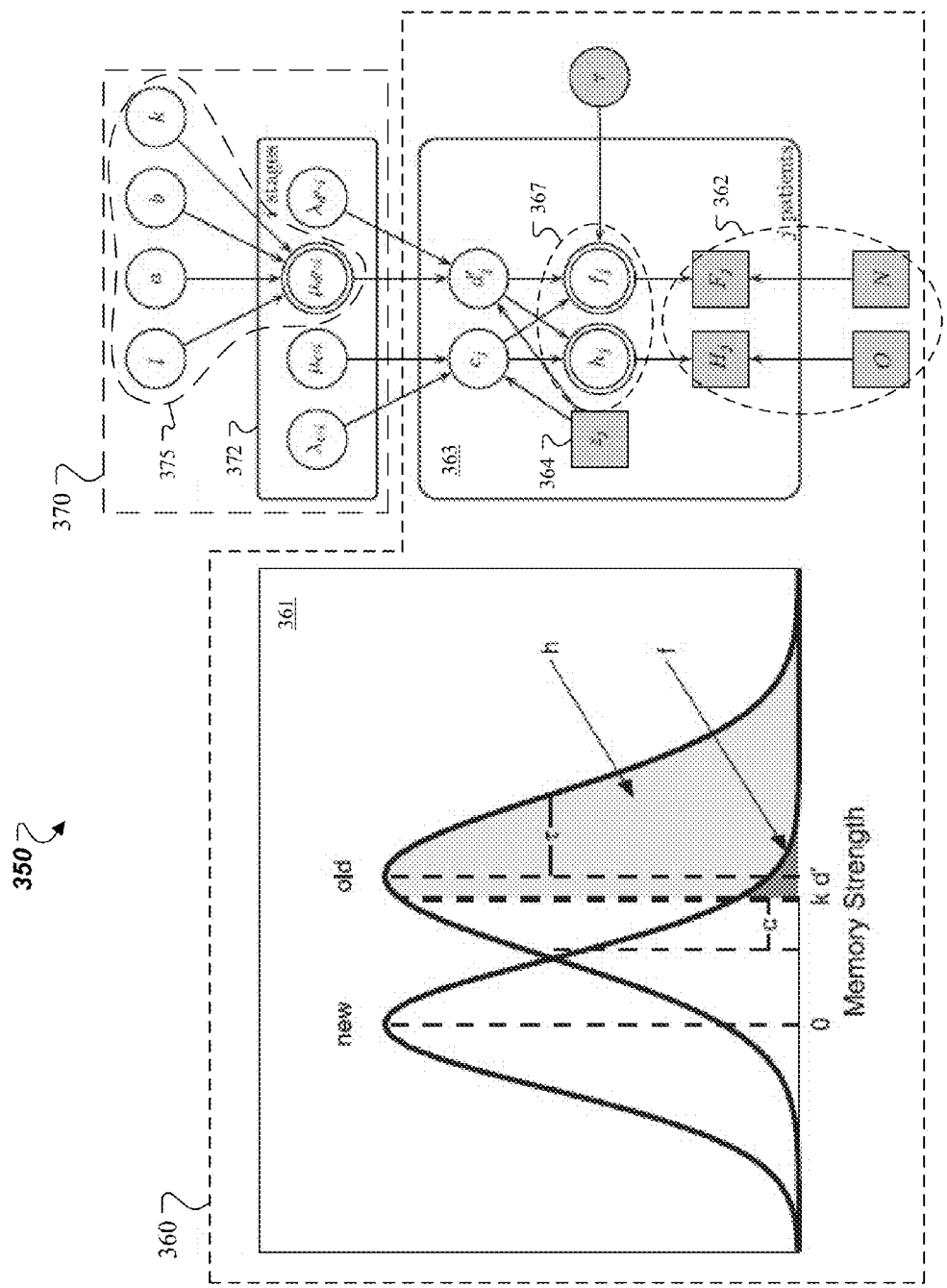
FIG. 3B shows an example utility used to estimate the cognitive processing parameters and relate them to the discrete-valued measure of functional severity.

HBCP Model for Delayed Recognition Memory:

FIG. 3B shows an example utility 350 used to generate a mapping of delayed recognition memory to functional ability. In some implementations, the utility 350 can be the cognition-to-function utility 150 described above in connection with FIG. 1. The utility 350 can include a cognitive processing modeler 360 and a mapper 370. The cognitive processing modeler 360 can include an SDT model 361 of the memory strength distributions for old and new list words that can be incorporated into the HBCP model 363. Each presented word evokes a memory strength, which the subject compares with their criterion level, k, for decision making. The SDT model 361 can predict that a subject will respond to a word that evokes a memory strength greater than "k" as an old word, whereas a word that evokes a memory strength less than or equal to "k" is responded to as a new word. The discriminability, d', is the difference between mean memory strengths of old and new list words, and indicates the memory gain from studying the old list words. The hit rate is the area, h, of the old word distribution, and lies above "k". The false alarm rate is the area, f, of the new word distribution, and also lies above "k". The response bias, c, for a subject is the distance between their criterion memory strength level, k, and the midpoint of their discriminability, d'. The response bias and discriminability can be assumed to be independent of each other. Because recognition memory experiments have found that the standard deviations of the old and new word distributions differ by about 25%, an unequal variance assumption can be incorporated into the SDT model 361.

Model Extension for Group and Individual Differences:

Unlike previous SDT applications to recognition memory data of ADRD patients, in this specification individual differences are modeled by introducing a parameter 364 reflecting the six functional severity levels (FAST stages 1 to 6), which influenced the response bias, $c_j$, and discriminability, $d'_j$ of each subject (patient), j. Each subject's discriminability and response bias parameters can be drawn from the distribution of values generated by the subject's FAST stage group. In this way, the HBCP model 363 allows different parameter values for individuals with the same FAST stage.

Model Extension for Predicting Changes in Discriminability:

Discriminability, d', between old and new words can be modeled by a psychophysical function 375 that makes d' a function of FAST stage severity. For FAST stage i, the mean discriminability is $$\mu_{d'i} = k + \left(\frac{l}{1 + ae^{bi}}\right),$$

where "k" corresponds to baseline discriminability, "l" corresponds to the potential change in discriminability across FAST severity levels, and "a" and "b" are parameters that control the shape of the psychophysical function. A sigmoid form of the psychophysical function 375 can be selected because the changes in discriminability between each of the FAST stages from 1 to 6 are nonlinear. The term in the denominator, $ae^{bi}$, can approach zero nonlinearly as one progresses from FAST stage 1 to 6, which maximizes the value of the numerator, 1, at FAST stage 6. Thus, the change in mean discriminability from baseline at FAST stage 1 will be maximal at FAST stage 6 and will approach it nonlinearly. The disclosed approach goes beyond simply testing for a significant difference in discriminability between FAST stages and models how discriminability changes with functional severity.

HBCP Graphical Model Implementation:

The hierarchical SDT model 361 can be combined with a Bayesian graphical model 363. In graphical models, nodes correspond to variables and their interdependencies show the causal relationships between the variables. In particular, graphical models can show how unobserved variables (e.g., parameters) generate observed variables (e.g., data). The practical advantage of graphical models is that Markov Chain Monte Carlo (MCMC) algorithms exist that can sample from the full joint posterior distribution of the parameters conditional on the observed data. In Bayesian statistics, the posterior is the probability distribution of unobserved values (often parameters) that results after a prior distribution has been updated by data.

In the Bayesian model 363, the shaded nodes represent observed/collected data, e.g., the results of the cognitive ability assessment 362, and the results of the functional ability assessment 364. The latter results 364 can correspond to the six functional severity levels (FAST stages 1 to 6), for instance. The un-shaded nodes represent unobserved/inferred data; the square nodes represent discrete variables; the circular nodes represent continuous variables; and double circled nodes represent deterministic variables. A deterministic variable is one whose result is defined by the values of other variables that point to the deterministic node. For example, if $h_j$ is a deterministic variable (node) that receives input from two other variables, $d'_j$ and $c_j$, then $h_j$ is determined by a function of $d'_j$ and $c_j$, which can be predefined for a particular implementation, or in some implementations can be defined by a user.

The HBCP graphical model 363 can determine the $j^{th}$ patient's discriminability and response bias parameters ($d'_j$ and $c_j$ nodes). These parameters generate the $j^{th}$ patient's predicted hit, $h_j$, and false-alarm, $f_j$, rates, 367, according to the SDT model 361. The hit rate can be expressed as $h_j = \Phi[(d'_j/2) - c_j]$ and the false-alarm rate as $f_j = \Phi[-[(d'_j/2) + c_j]/\tau]$, where τ=0.8, which arises from the unequal variance assumption. On the basis of these hit and false alarm rates 367 and the O=10 old and N=10 new words presented to each patient during the recognition task, the $j^{th}$ patient produces $H_j$ observed hits and $F_j$ observed false alarms 362, which follow binomial distributions parameterized by hit and false-alarm rates 367 and by their number of old and new words presented [$H_j$~binomial($h_j$,O), $F_j$~binomial($f_j$,N)]. Each FAST stage, i, has its own set of Gaussian distributions 372 for the discriminability d' and response bias "c" parameters, which are controlled by their mean, μ, and precision, λ ($\lambda=1/\sigma^2$) variables. These FAST stage group distributions 372 are implemented using an indicator variable, $z_j$, 364, which takes the value, 1, 2, . . . , 6 according to the $j^{th}$ patient's FAST stage. For a patient, j, its discriminability is distributed as $d_j$~Gaussian ($\mu_{d'zj}, \lambda_{d'zj}$) and its response bias is distributed as $c_j$~Gaussian ($\mu_{czj}, \lambda_{czj}$). Finally, the psychophysical function 375 determines the mean discriminability of FAST stage, i ($\mu_{d'i}$ node), which then updates the subject's discriminability, $d'_j$.

Bayesian Inference Generated by the HBCP Graphical Model and Clinical Data:

In some implementations, the mapper 370 can use a range of MCMC computational methods to obtain samples from the posterior distributions of the relevant parameters. In the current example case study, 10,000 posterior samples were collected to perform all analyses, after a burn-in of 1000 samples (samples collected but not used to approximate the posterior distribution of interest), using multiple chains to check convergence.

Figure 4:
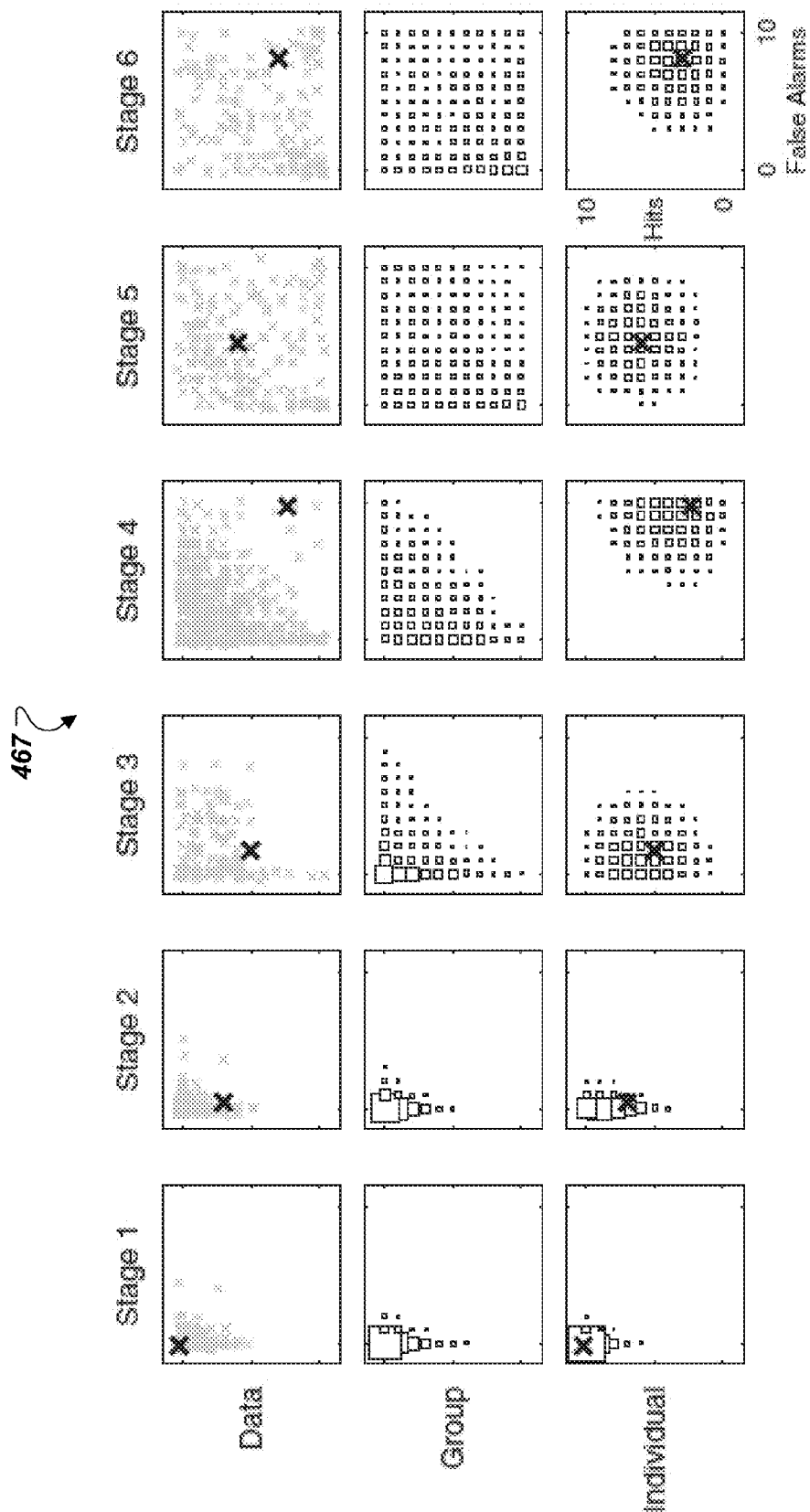
FIG. 4 shows examples of charts for observed delayed recognition memory task performance, as well as for estimated delayed recognition memory (hits and false alarms) for groups and individuals obtained using the example utility of FIG. 3B.

Posterior predictive distributions can assess the descriptive adequacy of the Bayesian model 363 by predicting what the data's distribution should be. FIG. 4 shows a set of charts 467 representing a posterior predictive analysis for the implemented HBCP model 363. Rows 1 to 3 correspond to the (1) observed delayed recognition data (y axis=hits, x axis=false alarms); (2) group-level (FAST stage) model inferences; and (3) individual-level model inferences 367, showing one patient per FAST stage, with their mean value marked as an "x". The hollow black squares show the distribution of predicted hits and false alarms for each FAST stage (column) For row 1, the gray x's are the patient-observed hits and false alarms 362. For row 2, the hollow black squares show the posterior predictive distribution of hits and false alarms at the group level (FAST stage); each square's area is proportional to its predictive mass. Comparison of rows 1 and 2 indicates that the group-level predictions match the observed data fairly closely, which is consistent with a well-fitting model. For row 3, the hollow black squares show the posterior predictive distribution of hits and false alarms 367 for a selected patient in each FAST stage; each square's area is proportional to its predictive mass for that patient in that FAST stage.

Note that the posterior predictive distributions of the individuals selected for FAST stages 4 to 6 represent outliers for their FAST stage groups. The use of an individual who is an outlier for a given group illustrates the point that one can concurrently examine both the group and the individual posterior predictive distributions. It also illustrates the point that the distribution of the individual outlier patient is different from that of the group and is more informative than simply using the group distribution for that individual. Specifically, one can see that the HBCP model 363's posterior predictive distribution of hits and false alarms 367 for any given selected individual outlier patients is a much better fit than the group-level predictions in row 2. The HBCP model 363's ability to characterize these individuals well, while concurrently describing group-level performance well, highlights an important advantage of the hierarchical approach for modeling individual differences.

Figure 5:
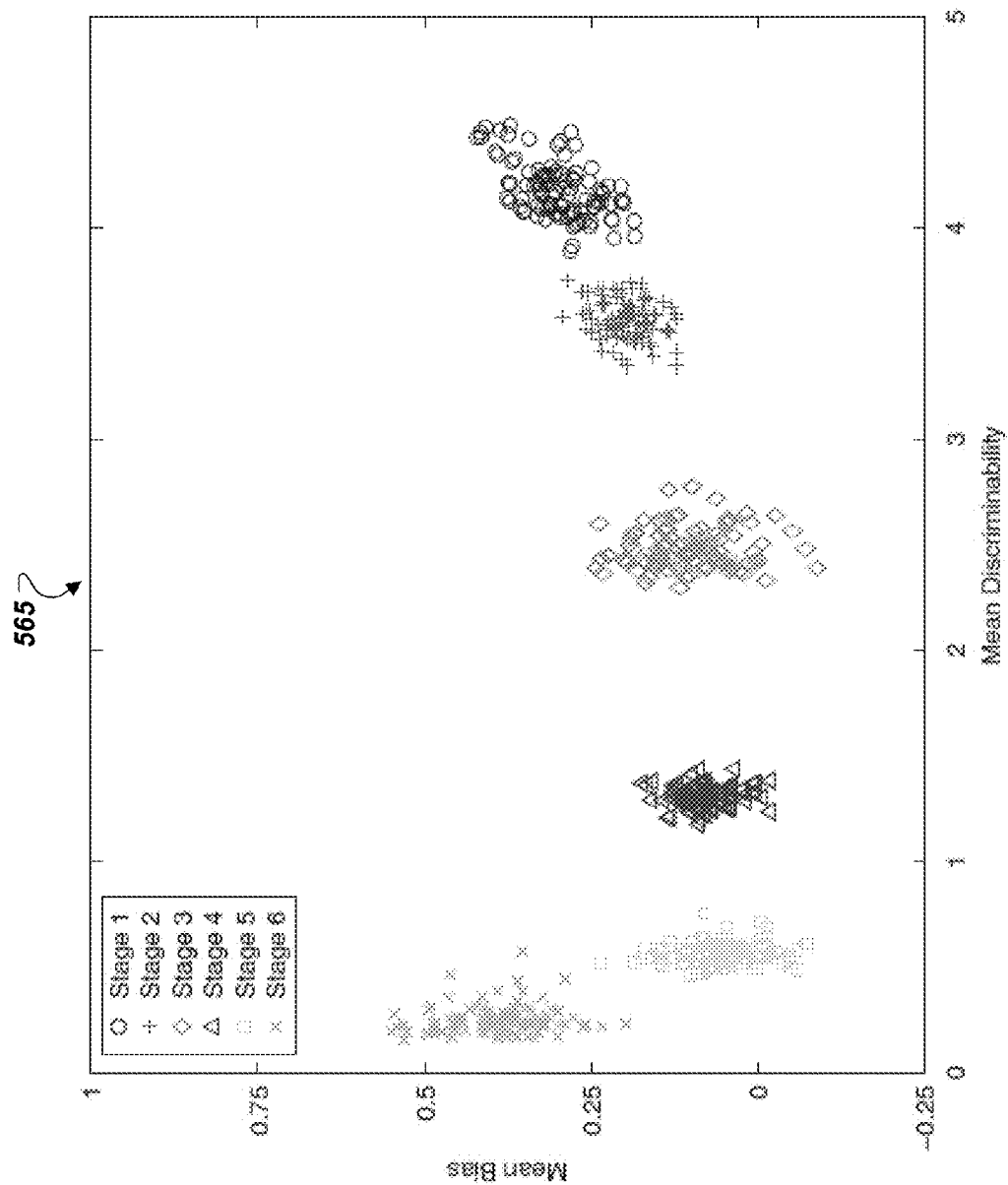
FIG. 5 shows an example of a chart of the group distributions for mean discriminability and mean response bias corresponding to a discrete-valued measure of functional severity that are obtained by using the example utility of FIG. 3B.

Assessing Discriminability, Response Bias, and Changes as ADRD Progresses:

FIG. 5 shows a chart 565 representing the joint posterior distributions of the discriminability and response bias parameters, d' and c, for each FAST stage. As the degree of functional impairment increases from FAST stages 1 (circles) to 6 (x's), discriminability between old and new list words decreases, and response bias shifts toward misses and false alarms being equally likely. However, response bias during FAST stage 6 (x's) shifts back toward that seen in normal aging patients (FAST 1), who make more misses than false alarms. According to the results shown in FIG. 5, the utility 350 used to model delayed recognition memory predicts that decision making—an executive function modeled by response bias—shifts toward unbiased responding during subjective cognitively related functional impairment and MCI (FAST 2 to 3). A surprising result was the shift back to biased responding similar to NCI individuals (FAST 1) during moderately severe dementia (FAST 6). FAST stage 6 patients have severe memory impairment, so that the memory strength distributions for the old and new wordlists can be similar. This loss of discriminability means that there is no memory signal to make a decision between old and new list words. However, judgment becomes more severely impaired as dementia severity progresses from FAST stages 4 to 6. This decline in judgment may shift the FAST stage 6 patient's decision-making criterion, k, to the right. This shift would yield a response bias, c, similar to that seen in NCI (FAST 1).

Figure 6:
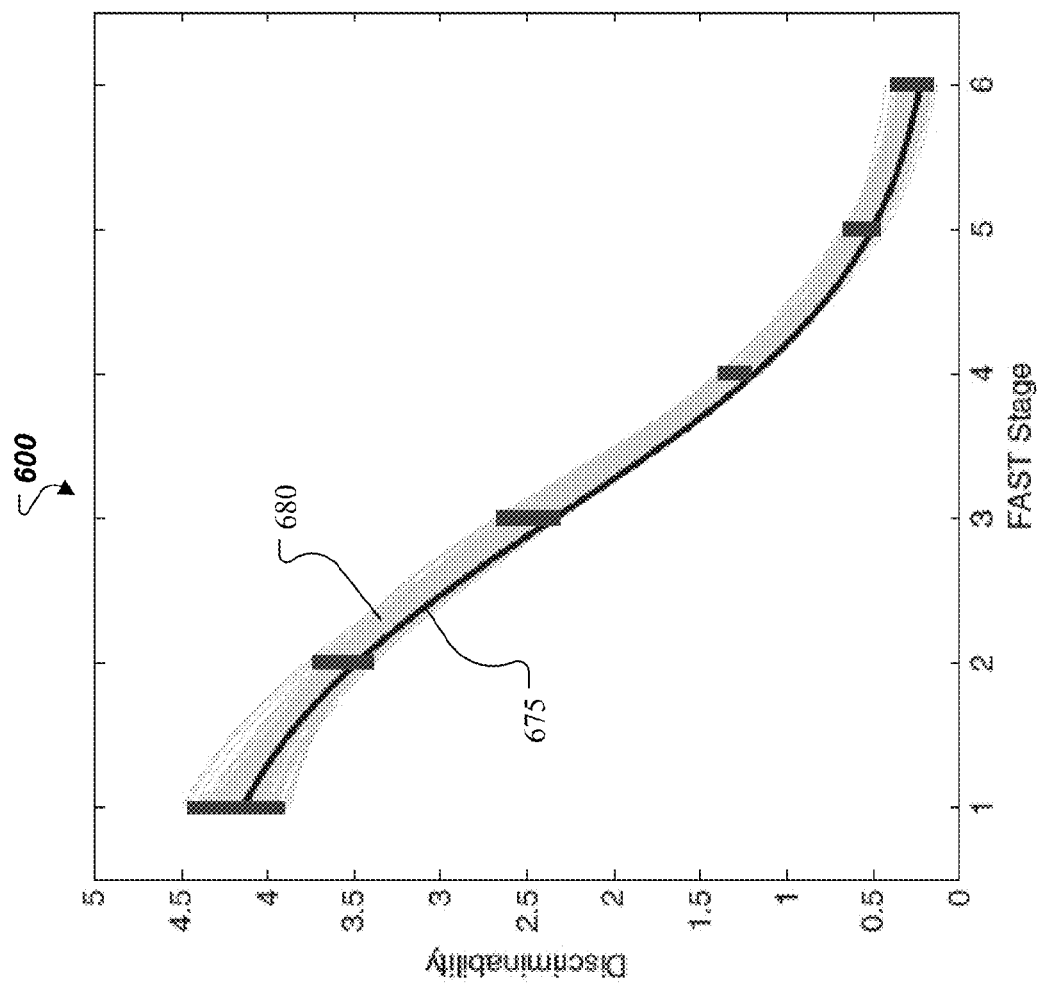
FIG. 6 shows an example of a map of discriminability to a continuous-valued measure of functional severity generated by using the example utility of FIG. 3B.

FIG. 6 shows a chart 600 representing the fit of the modeled relation between discriminability and the degree of impairment in functional capabilities (FAST stage). MCMC sampling of the discriminability values, $d'_i$, generated by the psychophysical function 375, was used to estimate the mean discriminability (black curve 675) and its 95% credible interval (gray curves 680) per FAST stage. This modeled relation uses fully Bayesian inference, which means that the joint distributions over the parameters of the sigmoid (k, l, a, b and FAST stage, i) and the group mean discriminability values, $\mu_{d'i}$, are concurrently inferred. The values on the x-axis that lie between the discrete FAST stage values—1 through 6—are inferred through the sigmoid function 375. It is these inferred values between the discrete FAST stage values along the x-axis that constitute the transformation of a discrete functional severity measure into a continuous one.

To predict $\mu_{d'i}$, the mean discriminability per FAST stage, any sampling method can be used, e.g., MCMC sampling, to sample the discriminability values, $d'_i$, generated by every possible sigmoid curve derived from the parameters of the psychophysical function 375, given the observed data 362, 364, and the HBCP/SDT model 361, 363. The black curve 675 shows the mean discriminability produced by the MCMC sampling method, and the gray curves 680 are the 95% credible intervals for the FAST stages. The uncertainty of the predicted mean discriminability was also estimated by random sampling of the discriminability values, $d'_i$, from their associated posterior distributions (gray curves 680). Both measures of uncertainty showed high reliability of the predicted mean discriminability of each FAST stage. The gray curves 680 show that the inferred continuous values on the x-axis lying between the discrete FAST stage values are reliable. In this sense, the sigmoid function 375 reveals the continuous, nonlinear decline in discriminability that is discovered via the quantized measurement using the discrete FAST stages (i.e., the right hand side of the cognition-to-function equation).

In addition, FIG. 6 shows that the relatively good fit between mean discriminability, $\mu_{d\eta}$, and the discrete FAST stages, plus the reliable inference of the mean discriminability values between the discrete FAST stages, means that the psychophysical function 375 used to model this relationship can help with interpolation, generalization and prediction of the severity of functional ability. In other words, this psychophysical function 375 enables tracing out trajectories of functional decline with respect to discriminability, and mapping these trajectories into statements about memory task performance and functional severity.

Figure 7:
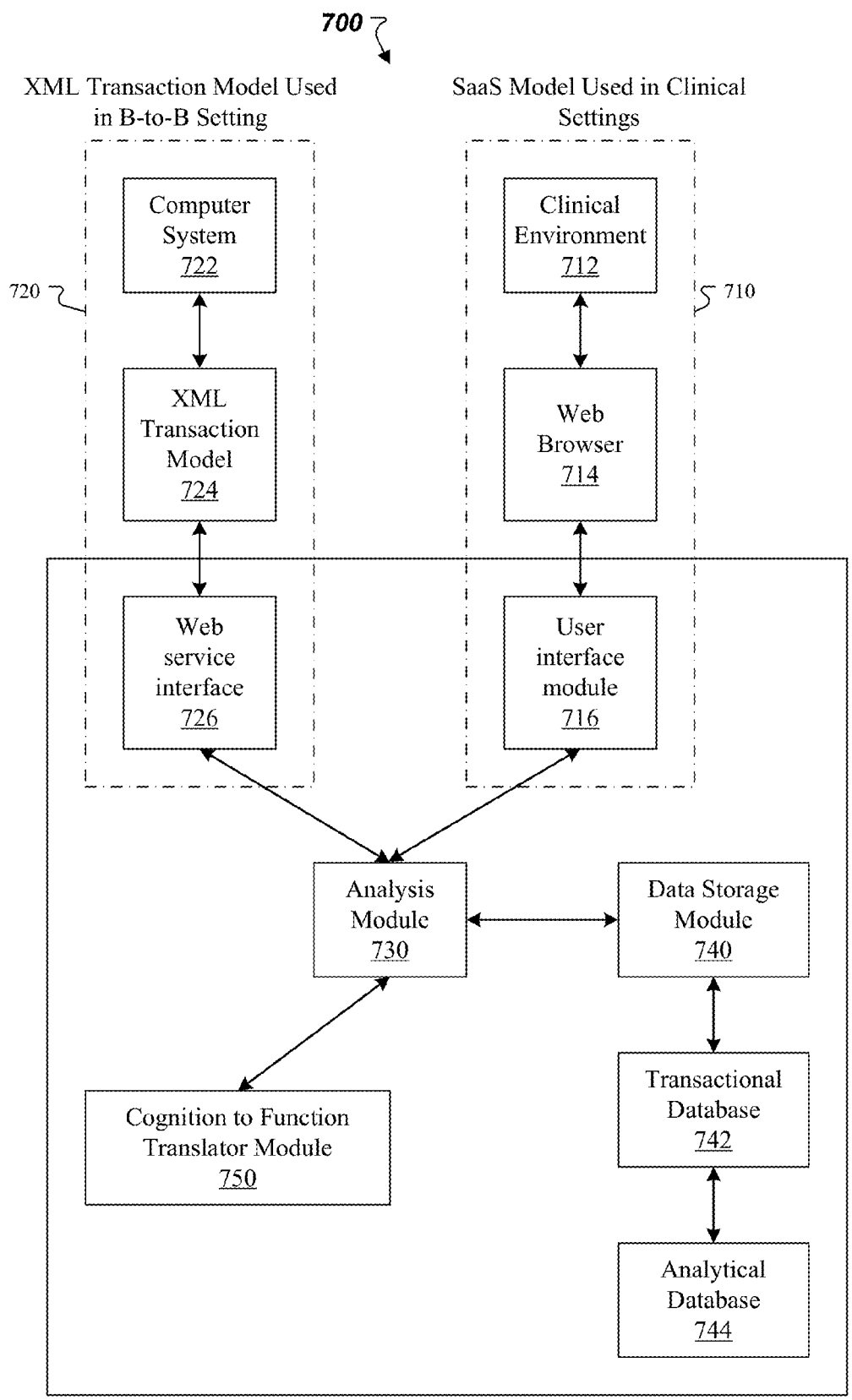
FIG. 7 shows another example system used to generate a mapping of cognitive to functional ability.

FIG. 7 shows another example system 700 used to generate a mapping of cognitive to functional ability. The example system 700 can perform a variety of functions including data analysis, storage and viewing, and remote access and storage capabilities useful for generating and using the analysis techniques described herein.

A Software as a Service (SaaS) model 710 can provide network based access to the software used to generate the mapping of cognitive to functional ability. This central management of the software can provide advantages, which are well known in the art, such as offloading maintenance and disaster recovery to the provider. A user, for example, a test administrator within a clinical environment 712, can access test administration software within the test administration system via a web browser 714 or other graphical user interface program (e.g., an application for a smart phone or a tablet computer). A user interface module 716 receives and responds to the test administrator interaction.

An XML transaction model used in a B-to-B setting 720 can also provide network based access to the software used to generate the mapping of cognitive to functional ability. A customer's computer system 722 can access software and interact with the test administration system using an eXtensible Markup Language (XML) transactional model 724. The XML framework provides a method for two parties to send and receive information using a standards-based, but extensible, data communication model. A web service interface 726 receives and responds to the customer computer system 722 in XML format. For example, an XML transactional model 724 can be useful for storage and retrieval of the structured data relating to the map of cognitive to functional ability.

An analysis module 730 analyses inputs from the web service interface 726 and the user interface module 716, and produces test results to send. The analysis module 730 uses a cognition-to-function translator module 750 to generate the map of cognitive to functional ability. The cognition-to-function translator module 750 can, for example, incorporate the methods described elsewhere in this specification, e.g., with respect to FIGS. 1, 2 and 3B.

A data storage module 740 transforms the test data collected by the user interface module 716, web service interface 726, and the resulting data generated by the cognition-to-function translator module 750 (e.g., the generated map of cognitive to functional ability) for permanent storage. A transactional database 742 stores data transformed and generated by the data storage module 740. For example, the transactional database 742 can keep track of individual writes to a database, leaving a record of transactions and providing the ability to roll back the database to a previous version in the event of an error condition. An analytical database 744 can store data transformed and generated by the data storage module 740 for data mining and analytical purposes.

As will be appreciated, the above described systems and techniques can be used in various applications, with individuals or groups in any of various states. For instance, a cognitive processing model can be used with a cognitive task, a discrete measure of functional severity (nominal, binary or ordinal), and a model of the mathematical form of the relation between cognition and function to develop a procedure to discover a continuous-valued functional severity measure from a cognitive measure and a discrete or ordinal functional one.

Embodiments of the subject matter and the functional operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer program products, i.e., one or more modules of computer program instructions encoded on a tangible program carrier for execution by, or to control the operation of, data processing apparatus. The tangible program carrier can be a propagated signal or a computer-readable medium. The propagated signal is an artificially generated signal, e.g., a machine-generated electrical, optical, or electromagnetic signal that is generated to encode information for transmission to suitable receiver apparatus for execution by a computer. The computer-readable medium can be a machine-readable storage device, a machine-readable storage substrate, a memory device, or a combination of one or more of them.

The term "data processing apparatus" encompasses all apparatus, devices, and machines for processing data, including by way of example a programmable processor, a computer, or multiple processors or computers. The apparatus can include, in addition to hardware, code that creates an execution environment for the computer program in question, e.g., code that constitutes processor firmware, a protocol stack, a database management system, an operating system, a cross-platform runtime environment, or a combination of one or more of them. In addition, the apparatus can employ various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub-programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processors of any kind of digital computer. Generally, a processor will receive instructions and data from a read-only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory can be supplemented by, or incorporated in, special purpose logic circuitry.

While this specification contains many implementation details, these should not be construed as limitations on the scope of the invention or of what may be claimed, but rather as descriptions of features specific to particular embodiments of the invention. Certain features that are described in this specification in the context of separate embodiments can also be implemented in combination in a single embodiment. Conversely, various features that are described in the context of a single embodiment can also be implemented in multiple embodiments separately or in any suitable sub-combination. Moreover, although features may be described above as acting in certain combinations and even initially claimed as such, one or more features from a claimed combination can in some cases be excised from the combination, and the claimed combination may be directed to a subcombination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems can generally be integrated together in a single software product or packaged into multiple software products.

Thus, particular embodiments of the invention have been described. Other embodiments are within the scope of the following claims. For example, the actions recited in the claims can be performed in a different order and still achieve desirable results.

What is claimed is:

1. A method comprising:
    receiving data regarding assessments of a cognitive ability and assessments of a functional ability;
    modeling one or more cognitive processes underlying the cognitive ability, based on the received data and a cognitive processing model, in accordance with a discrete-valued measure of the functional ability;
    generating a map of the one or more cognitive processes underlying the cognitive ability to a continuous-valued measure of the functional ability such that the generated map is anchored by the discrete-valued measure of the functional ability;
    storing the map of the one or more cognitive processes to the continuous-valued valued measure of the functional ability on a non-transitory computer-storage medium; and
    assessing, by a computer device based on the map of the one or more cognitive processes to the continuous-valued measure of the functional ability, continuous-values of the functional ability of one or more patients.

2. The method of claim 1, comprising:
    iteratively performing the actions of
        adjusting the cognitive processing model based on the map of the one or more cognitive processes to the continuous-valued measure of the functional ability,
        remodeling the one or more cognitive processes, based on the received data and the adjusted cognitive processing model, in accordance with the discrete-valued measure of the functional ability, and
        regenerating the map of the one or more cognitive processes to the continuous-valued measure of the functional ability,
    until convergence of the remodeling and the regenerating is obtained.

3. The method of claim 1, wherein the modeling comprises:
    indicating how the one or more cognitive processes predict the received data;
    estimating values of parameters of the one or more cognitive processes from indications by the cognitive processing model of how the one or more cognitive processes predict the received data; and
    grouping values of at least one of the parameters of the one or more cognitive processes in groups corresponding to values of the discrete-valued measure of the functional ability.

4. The method of claim 3, wherein the generating of the map comprises estimating a continuous functional relationship that fits the grouped values of the at least one of the parameters of the one or more cognitive processes and the values of the discrete-valued measure of the functional ability.

5. The method of claim 4, wherein the continuous functional relationship comprises a parametric psychophysical function having multiple parameters that control at least a baseline, potential change and a shape of the parametric psychophysical function.

6. The method of claim 4, wherein the estimating the reliability of the continuous functional relationship comprises one or more of Markov Chain Monte Carlo sampling, bootstrapping or permutation sampling.

7. The method of claim 3, comprising
    indicating individual predictions of the received data based on individual values of the at least one of the parameters of the one or more cognitive processes and group predictions of the received data based on grouped values of the parameters of the one or more cognitive processes, and
    comparing the indicated individual and group predictions to determine a cognitive difference of an individual associated with the individual prediction relative to a group of individuals associated with the group prediction.

8. The method of claim 3, wherein
the cognitive ability comprises a delayed recognition memory task,
the one or more cognitive processes underlying the delayed recognition memory task comprises latent cognitive processes including memory strength and judgment, and
a parameter of the memory strength comprises discriminability and a parameter of the judgment comprises response bias.

9. The method of claim 1, wherein the cognitive processing model comprises a combination of a signal detection theory model and a Bayesian analysis.

10. The method of claim 1, wherein the discrete-valued measure of the functional ability comprises one or more of the Clinical Dementia Rating Scale, the Alzheimer's Disease Cooperative Study Activities of Daily Living Scale or the Functional Assessment Staging Test Procedure.

11. The method of claim 1, wherein the one or more cognitive processes underlying the cognitive ability comprise at least one of a directly measurable cognitive process or a latent cognitive process, wherein the latent cognitive process is inferred from the received data.

12. The method of claim 1, wherein the functional ability is related to the cognitive ability.

13. The method of claim 1, wherein the assessing of the continuous-values of the functional ability of the one or more patients based on the map comprises determining a rate of change in the functional ability of the one or more patients.

14. The method of claim 1, wherein the assessing of the continuous-values of the functional ability of the one or more patients based on the map comprises monitoring continuous decline or improvement over time of the functional ability of the one or more patients.

15. A system comprising:
one or more hardware processors; and
a storage system comprising a non-transitory computer-storage medium, the storage system storing instructions that, when executed by the one or more hardware processors, cause the system to perform operations comprising:
receiving data regarding assessments of delayed recognition memory and assessments of a functional severity;
modeling discriminability as a parameter of memory strength and response bias as a parameter of judgment, where the memory strength and the judgment are latent cognitive processes underlying the delayed recognition memory, where the discriminability and response bias are modeled based on the received data and a cognitive processing model, in accordance with a discrete-valued measure of the functional severity;
generating a map of the discriminability to a continuous-valued measure of the functional severity such that the generated map is anchored by the discrete-valued measure of the functional severity;
storing the map of the discriminability to the continuous-valued measure of the functional severity; and
assessing, based on the map of the discriminability to the continuous-valued measure of the functional severity, continuous-values of the functional severity for one or more patients.

16. The system of claim 15, wherein the instructions, when executed by the one or more hardware processors, cause the system to iteratively perform operations comprising:
adjusting the cognitive processing model based on the map of the discriminability to the continuous-valued measure of the functional severity,
remodeling the discriminability and the response bias, based on the received data and the adjusted cognitive processing model, in accordance with the discrete-valued measure of the functional severity, and
regenerating the map of the discriminability to the continuous-valued measure of the functional severity,
until convergence of the remodeling and the regenerating is obtained.

17. The system of claim 15, where the operation of modeling comprises:
indicating how the discriminability and the response bias predict the received data;
estimating values of the discriminability and values of the response bias from indications by the cognitive processing model of how the discriminability and the response bias predict the received data; and
grouping the values of the discriminability and the values of the response bias in groups corresponding to values of the discrete-valued measure of the functional severity.

18. The system of claim 17, wherein the operation of generating the map comprises estimating a continuous functional relationship that fits the grouped values of the discriminability and values of the discrete-valued measure of the functional severity.

19. The system of claim 18, wherein the continuous functional relationship comprises a parametric psychophysical function having multiple parameters that control at least a baseline, potential change and a shape of the parametric psychophysical function.

20. The system of claim 18, wherein the operation of estimating the reliability of the continuous functional relationship comprises one or more of Markov Chain Monte Carlo sampling, bootstrapping or permutation sampling.

21. The system of claim 17, where the operations comprise:
indicating individual predictions of the received data based on individual values of the discriminability and the response bias and group predictions of the received data based on grouped values of the discriminability and the response bias, and
comparing the indicated individual and group predictions to determine a cognitive difference of an individual associated with the individual prediction relative to a group of individuals associated with the group prediction.

22. The system of claim 15, wherein the cognitive processing model comprises a combination of a signal detection theory model and a Bayesian analysis.

23. The system of claim 15, wherein the discrete-valued measure of the functional severity comprises one or more of the Clinical Dementia Rating Scale, the Alzheimer's Disease Cooperative Study Activities of Daily Living Scale or the Functional Assessment Staging Test Procedure.

24. The system of claim 15, wherein the functional severity is related to the delayed recognition memory.

25. The system of claim 15, wherein the operation of assessing the continuous-values of the functional severity of the one or more patients based on the map comprises determining a rate of change in the functional severity of the one or more patients.

26. The system of claim 15, wherein the operation of assessing the continuous-values of the functional severity of the one or more patients based on the map comprises monitoring continuous decline or improvement over time of the functional severity of the one or more patients.

* * * * *